H. A. CHAPIN.
Carbureters.
No. 6,070. Reissued Sept. 29, 1874.
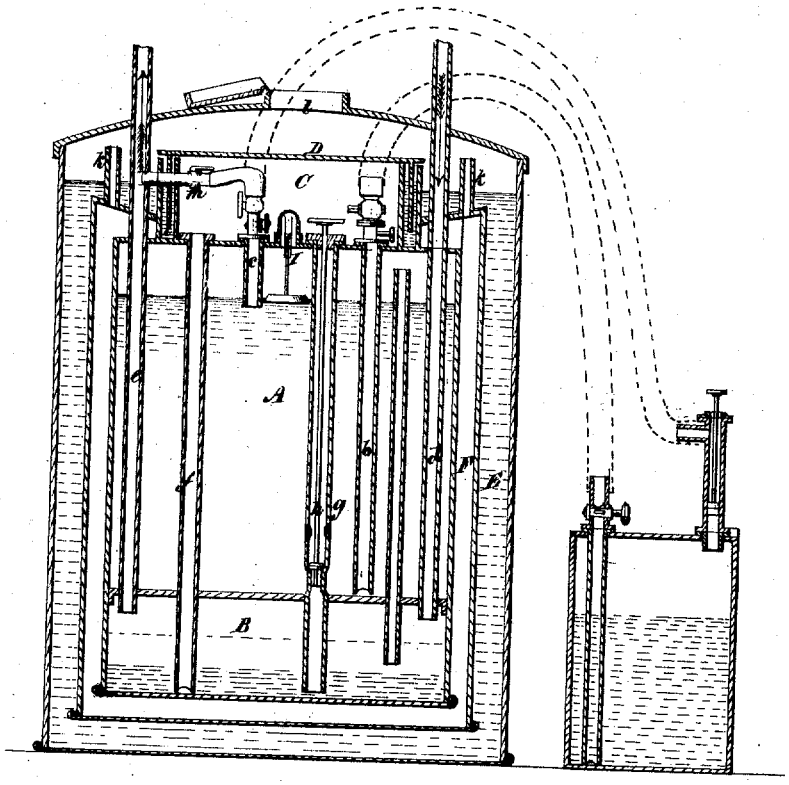
Witnesses.
Fred Haynes
R. G. Rahm
Henry Albert Chapin
THE GRAPHIC CO. PHOTO-LITH. 39 & 41 PARK PLACE, N.Y.

UNITED STATES PATENT OFFICE.

HENRY ALBERT CHAPIN, OF NEW YORK, N. Y.

IMPROVEMENT IN CARBURETERS.

Specification forming part of Letters Patent No. 111,175, dated January 24, 1871; reissue No. 6,070, dated September 29, 1874; application filed October 23, 1871.

*To all whom it may concern:*

Be it known that I, HENRY ALBERT CHAPIN, of the city, county, and State of New York, have invented a new and useful Improvement in Carbureting Apparatus, of which the following is a full, clear, and exact description, reference being had to the accompanying drawing forming part of this specification, and which represents a sectional elevation of a carbureting apparatus having my improvement applied to it.

My invention, which is mainly designed for the carbureting of street-gas, consists in a novel combination, within the carbureter, of the regulating-valve and its connections, for controlling the discharge of the liquid from the reservoir to the carbureting-chamber, whereby said valve may be adjusted from the exterior without making a break in the walls of the carbureter, thereby reducing the risk of accident by leakage.

The invention also consists in a certain combination, with the tank or reservoir, of a chamber provided with a sealed lid or cover, in combination with the valve, by which the supply from the tank to the carbureting-chamber is regulated and made capable of operation from within said sealed chamber, whereby further protection against accident from leakage is obtained; also escaping vapor retained within the carbureter.

The invention likewise consists in a combination, with said sealed chamber, of the several pipes or attachments connected with the supply and draft of the liquid to and from the tank and carbureting-chamber, for the purposes already cited, and so that, on opening the sealed chamber, the various attachments or connections are exposed for inspection, adjustment, or repair.

The invention also consists in a combination, with the pipe which carries off the carbureting-gas from the apparatus, of a pipe or connection fitted with a cock or valve, and establishing communication between said gas-pipe and an air-escape pipe or opening in the upper portion of the tank, whereby any condensed air and vapor with which it may be charged, produced in filling the tank, may be discharged into the gas-pipe.

The invention also comprises, in combination with an outer water or safety jacket, an interposed air-circulating chamber between said jacket and the carbureter proper, which it incloses, said chamber essentially differing from a confined air-space by being provided with suitable openings or ducts, to provide for a free circulation of air through it, and for carrying off as rapidly as formed any vapor leaking into said chamber, or otherwise avoiding any excessive and dangerous accumulation of vapor therein.

Referring to the accompanying drawing, A represents the tank or reservoir of the apparatus, into which the carbureting-liquid is entered and drawn off therefrom, or surplus and refuse removed, as required, by means of a tube, *b*, arranged to project through the top of the tank down to nearly the bottom thereof. To effect the filling of the tank A, an air-escape or vacuum-tube, *c*, may also be used, the same being likewise arranged to project through the top of the tank, but only entering to a limited distance down within it. These tubes *b* and *c* may be provided with suitable cocks or valves on their exterior or upper projecting ends, and be connected, respectively, by supplementary pipes with a dip-pipe and pump, attached to or forming part of a filling-can, so that the pump may first be worked to produce a vacuum within the tank A, and afterward to force the liquid from the can into the tank. This provides for the charging of the tank in a rapid manner, and from a level which is considerably below the tank; also for the drawing off of the liquid or refuse, when required.

Any other filling and drawing-off means, however, may be employed, and in some cases the tube *c* be dispensed with; or, when used, instead of operating as a vacuum-pipe in connection with a pump it may, under a different mode of filling, be employed as an escape-pipe for condensed air, produced in the upper portion of the tank during the process of filling.

In such case I connect such tube *c* by a pipe or connection, *m*, having a cock or valve, with the pipe *e*, which carries off the carbureted gas into the building. By this connection *m* all condensed air and vapor with which it may be charged is passed off into the pipe *e* for use along with the gas. B is the carbureting chamber, and *d* the gas-inlet pipe, which latter, together with the gas-outlet pipe *e*, is likewise preferably disposed to run up through the tank A. Projecting up within said tank are also the draw-off pipe *f* from the carbureting-chamber B, and the supply-tube *g* thereto, and connection by which the regulating-valve *h* is operated to control the supply of liquid from the tank A to the carbureting-chamber. I is a float-indicator, for ascertaining the level of the liquid in the tank. Said indicator, like the tubes *b* and *c*, the draw-off pipe *f* from the carbureting-chamber B, and the regulating-valve *h*, which controls the supply to the latter, are all in communication with and accessible from a chamber, C, arranged on top of the tank, and provided with a lid, D, which is sealed, as by a glycerine, mercurial, or other fluid joint, *i*. The arrangement of the regulating-valve *h* and its connections all within the carbureter proper, and without making a break in its walls or surrounding chambers to effect the adjustment of the valve from the exterior, is an important feature in this invention, inasmuch as it reduces the liability of leakage, while the connection of the same, and of the filling and drawing-off attachments and indicator all within the chamber C, under cover of the sealed lid, as described, not only retain vapor leaking past said attachments or connections within the carbureter proper, but provide for a ready accessibility to said connections by simply removing the sealed lid D. E is a safety water-jacket or chamber surrounding the whole structure, and F an interposed air-circulating chamber or space between said water-jacket and the carbureter proper, to form an additional safeguard. This air-chamber insulates, as it were, the carbureter, the same being arranged around its sides and bottom or bottom and top, and the water-jacket E similarly insulates said air-chamber, which latter is provided with vents or pipes *k k*, that in connection with an opening, *l*, made in the top of the water-case, serve to keep up a circulation of air within the chamber F. This provides for the carrying off of any liquid or vapor that might escape from the carbureter into said chamber, instead of allowing it to accumulate for mixture with a fixed supply of air till a dangerous or explosive condition is reached.

What is here claimed, and desired to be secured by Letters Patent, is—

1. The combination, with the tank or reservoir A and carbureting-chamber B, of the valve *h*, by which the supply of liquid from the former to the latter is regulated, said valve and its working device or connections being arranged within the carbureter or tank thereof, and made capable of operation from the exterior, without a break in the walls endangering leakage of liquid from the tank to the exterior of the carbureter, substantially as specified.

2. The combination, with the tank A, of the chamber C, provided with a sealed lid or cover, as described, and the valve by which the supply from the tank to the carbureting-chamber is regulated and made capable of operation from within the sealed upper chamber C, substantially as specified.

3. The combination, with the sealed upper chamber, of the several pipes or connections by which the liquid is supplied to and drawn from the tank A and carbureting-chamber B, essentially as herein set forth.

4. The combination, with the gas-pipe *e* and air-escape tube *c*, of the connection *m*, substantially as and for the purpose herein described.

5. The combination, with the carbureter and with an outer water-case or jacket, E, of an air-circulating space or chamber, F, provided with vents or ducts, substantially as and for the purpose or purposes specified.

HENRY ALBERT CHAPIN.

Witnesses:

FRED. HAYNES,
R. E. RABEAU.